(12) United States Patent
Beer et al.

(10) Patent No.: US 8,969,071 B2
(45) Date of Patent: Mar. 3, 2015

(54) PASSIVE CHIP-BASED DROPLET SORTING

(75) Inventors: Neil Reginald Beer, Pleasanton, CA (US); Abraham P. Lee, Irvine, CA (US); Andrew C. Hatch, Irvine, CA (US); Jeffrey S. Fisher, Irvine, CA (US)

(73) Assignees: Lawrence Livermore National Security, LLC, Livermore, CA (US); The Regents of the University of California, Oakland, CA (US)

( * ) Notice: Subject to any disclaimer, the term of this patent is extended or adjusted under 35 U.S.C. 154(b) by 1156 days.

(21) Appl. No.: 12/938,715

(22) Filed: Nov. 3, 2010

(65) Prior Publication Data

US 2012/0091059 A1  Apr. 19, 2012

Related U.S. Application Data

(60) Provisional application No. 61/392,784, filed on Oct. 13, 2010.

(51) Int. Cl.
*C12M 3/00* (2006.01)
*C12M 1/00* (2006.01)
(Continued)

(52) U.S. Cl.
CPC .......... *C12M 47/04* (2013.01); *B01L 3/502761* (2013.01); *B01L 7/52* (2013.01);
(Continued)

(58) Field of Classification Search
CPC .......... B81B 1/00; C12M 1/00; G01N 11/00; G01N 19/00; G01N 2015/02; G01N 2015/0205; G01N 2015/0238; G01N 2015/0255
USPC ......... 210/804, 606, 634, 639, 645, 660, 511, 210/321.6, 203, 196, 243, 153, 748.01, 210/748.02, 748.05; 435/283.1, 287.1, 6.1, 435/6.12, 287.2, 287.3, 288.5; 422/20, 127, 422/128, 129, 82, 501–504, 527, 551; 204/601; 436/53, 94, 174, 180
See application file for complete search history.

(56) References Cited

U.S. PATENT DOCUMENTS 8,528,589 B2 * 9/2013 Miller et al. ............... 137/487.5
2002/0058332 A1 * 5/2002 Quake et al. ............... 435/288.3
(Continued)

OTHER PUBLICATIONS

K. Khanafer et al, "Isothermal Surface Production and Regulation for High Heat Flux Applications Utilizing Porous Inserts". International Journal of Heat and Mass Transfer 44 (2001) 2933-2947. Department of Mechanical Engineering, Ohio State University, Columbus, OH 43210, USA. Received Oct. 26, 1999, received in revised from Oct. 9, 2000.

(Continued)

*Primary Examiner* — Walter D Griffin
*Assistant Examiner* — Cameron J Allen
(74) *Attorney, Agent, or Firm* — Eddie E. Scott (57) ABSTRACT

An apparatus for passive sorting of microdroplets including a main flow channel, a flow stream of microdroplets in the main flow channel wherein the microdroplets have substantially the same diameter and wherein the flow stream of microdroplets includes first microdroplets having a first degree of stiffness and second microdroplets having a second degree of stiffness wherein the second degree of stiffness is different than the first degree of stiffness. A second flow channel is connected to the main flow channel for the second microdroplets having a second degree of stiffness. A separator separates the second microdroplets having a second degree of stiffness from the first microdroplets and directs the second microdroplets having a second degree of stiffness into the second flow channel.

9 Claims, 8 Drawing Sheets

(51) Int. Cl.
*B01L 3/00* (2006.01)
*B01L 7/00* (2006.01)

(52) U.S. Cl.
CPC .. *B01L2200/0652* (2013.01); *B01L 2300/0864* (2013.01); *B01L 2300/168* (2013.01); *B01L 2400/084* (2013.01)
USPC ..... 435/287.2; 435/6.1; 435/6.12; 435/287.3; 435/288.5; 422/82; 422/501; 422/502; 422/504; 422/527; 210/748.01; 210/253; 210/143; 210/321.6; 204/601

(56) References Cited

U.S. PATENT DOCUMENTS

2005/0207940 A1* 9/2005 Butler et al. .................... 422/73
2007/0034270 A1* 2/2007 Yang et al. .................... 137/833

OTHER PUBLICATIONS

Monika Suchanek et al, "Photo-Leucine and Photo-Methionine Allow Identification of Protein-Protein Interactions in Living Cells". 2005 Nature Publishing Group. Max Planck Institute of Molecular Cell Biology and Genetics, Pfotenhauerstr, 108, D-01307 Dresden, Germany. Published online Mar. 23, 2005, pp. 1-7.

Eric N. Salgado et al, "Metal-Mediated Self-Assembly of Protein Superstructures: Influence of Secondary Interactions on Protein Oligomerization and Aggregation". Department of Chemistry and Biochemistry, University of California, San Diego, 9500 Gilman Drive, La Jolla, California 92093 JACS Communications, published on web Apr. 19, 2008. Received Feb. 18, 2008. American Chemistry Society 2008, pp. 6082-6084.

Stratis Avrameas et al, "The Cross-Linking of Proteins with Glutaraldehyde and Its Use for the Preparation of Immunoadsorbents". Laboratoire des Chimie des Proteines, Institut de Recherches Scientifiques sur le Cancer, Villejuif, France. Immunochemistry. Pergamon Press 1969. vol. 6, pp. 53-66. Printed in Great Britain.

Guillaume Lemercier et al, "Inducing and Sensing Protein-Protein Interactions in Living Cells by Selective Cross-Linking". Angewandte Chem. Int. Ed. 2007, pp. 4281-4284. © 2007 Wiley-VCH Verlag GmbH & Co. KGaA, Weinheim.

Justin T. Russell et al, "Self-Assembly and Cross-Linking of Bionanoparticles at Liquid-Liquid Interfaces". Angewandte Chem. Int. Ed. 2005, 44, 2420-2426. © 2005 Wiley-VCH Verlag GmbH & Co. KGaA, Weinheim.

* cited by examiner

PASSIVE CHIP-BASED DROPLET SORTING

CROSS-REFERENCE TO RELATED APPLICATIONS

The present application claims benefit under 35 U.S.C. §119(e) of U.S. Provisional Patent Application No. 61/392,784 filed Oct. 13, 2010 entitled "Passive Chip-Based Droplet Sorting," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to droplet sorting and more particularly to a system for passive sorting of microdroplets in a microfluidic system.

2. State of Technology

United States Published Patent Application No. 2008/0053205 for droplet-based particle sorting provides the following state of technology information: "The present invention relates to droplet-based particle sorting. According to one embodiment, a droplet microactuator is provided and comprises: (a) a suspension of particles; and (b) electrodes arranged for conducting droplet operations using droplets comprising particles. According to another embodiment, a droplet microactuator is provided and comprises a droplet comprising a single particle in the droplet. According to yet another embodiment, a method of transporting a particle is provided, wherein the method comprises providing a droplet comprising the particle and transporting the droplet on a droplet microactuator. According to a still further embodiment, a method of providing a droplet comprising a single particle is provided, wherein the method comprises: (a) providing a droplet comprising suspension of particles; (b) dispensing a droplet from the droplet of (a) to provide a dispensed droplet; and (c) determining whether the dispensed droplet comprises a single particle and/or a desired particle type."

U.S. Pat. No. 6,941,005 for monitoring and control of droplet sorting provides the following state of technology information:

A. Flow Cell Chamber
 One component of the system of the present invention, useful in the method of the present invention is a cell sorter 100 which provides for sorting of cells or particles in a suspension which are contained in a sample reservoir 102. The suspension is forced into a flow cell chamber 104 where sheathing fluid from a sheathing fluid reservoir 106 surrounds the sample as the sample enters the flow cell 104 from the sample tubing. This combination of sheath fluid and sample focuses the suspension into a serialized order in the resulting stream. The flow cell 104 provides an analysis point where the focused sample intersects a laser beam 108. The differences between the sample and sheath described above are detected in the flow cell 104.

B. Droplet Generator
 A droplet generator 114 is also included as a further component of the present invention. The droplet generator 114 perturbs the jet. By doing so, waves of undulations travel down the jet at the velocity of the jet. Preferably, a piezoelectric crystal is utilized to accomplish perturbation of the jet. The frequency of perturbation is set by a frequency generator (not shown), and may be varied as determined by one of skill in the art. The drive amplitude is set by an amplifier (not shown). The jet forms as the stream is forced through the exit nozzle 112 and breaks into droplets at the droplet generator drive frequency.
 The elapsed time between the time the sample is detected by the laser 108 in the flow cell 104 to the time that the stream is charged is called the delay time. The delay time must match the transit time of the desired sample from the analysis point to the last attached stream segment 116. The stream configuration must place the last attached stream segment 116 in the same position as the sample to ensure good sorting results. The stream configuration is manipulated in the present invention.

C. Detectors
 Another component useful in the present invention is a detection apparatus 118, which monitors the stream for specific particles and provides a characterization of the contents of the stream. Typically, the suspension and the sheath fluid stream 110 typically flow into a cuvette (not shown), which is illuminated by a light source 108. Preferably, the cuvette is present in a visualization chamber or portion of the flow cell 104. However, other chambers may be utilized to contain the suspension to be analyzed and may be selected by one of skill in the art. Suitable light sources include, without limitation, arc lamps, lasers, light bulbs, light emitting diodes (LED), among others. Typically, the light source 108 operates in a continuous mode.

D. Imaging Means
 A further component of the present invention includes an imaging means 38 (See FIGS. 6 through 12) to capture an image of the jet below the nozzle 112 according to the present invention. The imaging means can be located in a variety of positions to capture one or more views of the jet, but is preferably located at the droplet forming region 32 (see FIG. 1A) in the performance of this invention. A variety of imaging means are known in the art and can be utilized in the present invention and include the imaging means described herein.
 When the optical source or light field 120 illuminates the jet 110 below the nozzle 112, it strobes light at a frequency that is the same as the frequency of the droplet generator 114, e.g., the piezo oscillator, of the flow cytometer 100. The light field 120 can strobe light at the same frequency as the oscillator. In one embodiment, the imaging means is operated at a frequency of about 0.6 to about 100 kilohertz; however the frequency may be adjusted by one of skill in the art as needed.

E. Means for Generating the Numerical Standard and Sample Averages
 Typically, the image of the jet (see FIG. 2B) contains noise. Typically, the noise present in the images is generated by the optical illumination source or light field 120. However other components of the instrument can generate undesirable nose in the images. By reducing or eliminating the noise, a more accurate representation of the jet can be obtained. Thus, in order to obtain an accurate image of the jet to be analyzed, the residual noise present in the images of the jet should be eliminated or minimized. Typically, the noise is eliminated by subtracting a background image. The present invention therefore provides for obtaining one or more background images that contain noise (see FIG. 2A). The background images are typically obtained with no sheath or suspension fluid flow present. In order to obtain an accurate background image, multiple images of the background without sheath or suspension fluid flow are obtained. Preferably, about 5 or more background images are obtained. More preferably, about 5 to about 40 background images are obtained. Even more preferably, about 5 to about 10 background images are obtained. Most preferably, about 10 background images are obtained. The multiple background images can optionally be averaged to obtain a background image that is then used according to the invention.

Once the background image and image of the jet are obtained and the same enhanced, the background image is subtracted from the image of the jet to remove noise. See FIG. 2C. If the background image and image of the jet are of the same size, no additional manipulations may be required prior to subtracting the background image from the image of the jet. Conventional and useful noise reduction techniques are also described in the text of Tou and Gonzalez, cited above. If necessary, the images of the jet, before and after background subtraction, can be stored for manual or computer-assisted comparisons at a later date. Alternatively and preferably, the images are instantly obtained and displayed on a monitor. An advantage of the present invention however includes optimizing storage on a computer or optimizing the time required to display on a monitor and instantly processing the images according to the following without storing the same for later use.

G. Adjusting Means

In order to maintain a stable sort, the system can be adjusted prior to and during sorting the particles of the suspension. If a significant deviation of sample average from reference standard is detected, the method involves an adjusting step, in which the processor is programmed to gives commands to the sample pressure regulator, the sheath pressure regulator and/or the piezo oscillator to force the deviant averages back to the reference standard representative of a sort in known, stable and desirable condition. If unable to do so, the processor then issues other commands to the sample pinch, sheath pinch, deflection voltage, stream charge and the user interface to stop the sorting and alerts the user.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for passive sorting of microdroplets in a microfluidic system. The system does not require a measurement step as in other optic or electrically controlled sorters. Stiffness and viscosity of the droplets as the droplet contents change and sorting is accomplished through changes in shear forces which are controlled by device bifurcation junction geometry and flow rate. One embodiment of the present invention provides an apparatus for passive sorting of microdroplets including a main flow channel, a flow stream of microdroplets in the main flow channel wherein the microdroplets have substantially the same diameter and wherein the flow stream of microdroplets includes first microdroplets having a first degree of stiffness and second microdroplets having a second degree of stiffness wherein the second degree of stiffness is different than the first degree of stiffness, a second flow channel connected to the main flow channel for the second microdroplets having a second degree of stiffness, and a separator for separating the second microdroplets having a second degree of stiffness from the first microdroplets and directing the second microdroplets having a second degree of stiffness into the second flow channel. Another embodiment of the present invention provides a method of passive sorting of microdroplets including the steps of providing a main flow channel, providing a flow stream of microdroplets in the main flow channel wherein the microdroplets have substantially the same diameter and wherein the flow stream of microdroplets includes first microdroplets having a first degree of stiffness and second microdroplets having a second degree of stiffness wherein the second degree of stiffness is different than the first degree of stiffness, providing a second flow channel connected to the main flow channel for the second microdroplets having a second degree of stiffness, and providing a separator for separating the second microdroplets having a second degree of stiffness from the first microdroplets and directing the second microdroplets having a second degree of stiffness into the second flow channel.

The present invention has use in biowarfare detection applications including identifying, detecting, and monitoring bio-threat agents that contain nucleic acid signatures, such as spores, bacteria, viruses etc.; in biomedical applications including tracking, identifying, and monitoring outbreaks of infectious disease including emerging, previously unidentified and genetically engineered pathogens; in automated processing, amplification, and detection of host or microbial and viral DNA or RNA in biological fluids for medical purposes; high throughput genetic screening for drug discovery and novel therapeutics; genetic screening for oncology, disease, and personal genomics; compound discovery, proteomics, crystallography, and other research applications; and in forensic applications; automated processing, amplification, and detection of DNA in biological fluids for forensic purposes; and explosives detection and chemical processing.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Microfluidic devices are poised to revolutionize environmental, chemical, biological, medical, and pharmaceutical detectors and diagnostics. "Microfluidic devices" loosely describes the new generation of instruments that mix, react, count, fractionate, detect, and characterize complex gaseous or liquid-solvated samples in a micro-electro-mechanical system (MEMS) circuit manufactured through standard semiconductor lithography techniques. These techniques allow mass production at low cost as compared to previous benchtop hardware. The applications for MEMS devices are numerous, and as diverse as they are complex.

As sample volumes decrease, reagent costs plummet, reactions proceed faster and more efficiently, and device customization is more easily realized. By reducing the reaction volume, detection of target molecules occurs faster through improved sensor signal to noise ratio over large, cumbersome systems. However, current MEMS fluidic systems may only be scratching the surface of their true performance limits as new techniques multiply their sensitivity and effective throughput by ten, a hundred, or even a thousand times.

The present invention provides a method of enhancing a microfluidic detector's limits and increasing its throughput by passively sorting droplets that contain positive reaction products from those that don't, and allow microfluidic emulsion-based instrumentation systems to function well within the Poisson-regime, increasing the sensitivity down to single-copy levels and the accuracy of the instrument without sacrificing device throughput.

Microfluidic monodisperse droplet generators exist in the art and employ various methods to produce continuous streams of droplets of identical size for use as chemical reactors or optical detectors in labon-chip applications. These systems are very robust and efficient at generating the droplets, but they have no method for automatically sorting out droplets whose fluidic properties change based on the chemical reactions undergone in some or all of the manufactured droplets.

The system of the present invention provides a microfluidic architecture optimized to use the applied velocity flow (and shear) fields to allow a "passive" sorting of droplets, where we use the term passive to signify that no additional sorting steps or interventions are required such as optical interrogation, applied electromagnetic force fields (such as dielectrophoresis, or DEP), and no applied pressure fields (fluidic pressure pulses or optical trapping pressures). The sorting method we describe here eliminates the expense, complexity, lowered throughput, and reliability issues associated with those previous "active" sorting techniques.

The present invention provides an apparatus for passive sorting of microdroplets including a main flow channel, a flow stream of microdroplets in the main flow channel wherein the microdroplets have substantially the same diameter and wherein the flow stream of microdroplets includes first microdroplets having a first degree of stiffness and second microdroplets having a second degree of stiffness wherein the second degree of stiffness is different than the first degree of stiffness. A second flow channel is connected to the main flow channel for the second microdroplets having a second degree of stiffness. A separator separates the second microdroplets having a second degree of stiffness from the first microdroplets and directs the second microdroplets having a second degree of stiffness into the second flow channel.

As the droplet reactors are typically employed, they contain solvated chemicals intended to react in the droplets to serve a desired analytical purpose, such as chemical or biological species detection, polymer assembly, crystallography, nanoparticle synthesis, etc. All of these desired chemical reactions change the ratio of reactants to products internally in the droplets undergoing successful reactions. For a large number of the current and future microfluidic uses of droplets, the change in the quantities and ratios of reactants and products, especially in large molecule assembly processes such as polymerization and PCR—these changes alter the viscosity of the droplets and their mechanical "stiffness" (the reciprocal of their compliance, "stiffness" has units of N/m and is essentially a spring constant.)

Designing a properly bifurcated flow channel junction that has been optimized for the monodisperse droplet size and carrier fluid will allow for the selection of only the droplets that have a sufficient quantity of post-amplified or reacted material to change the droplet's viscosity, and hence its stiffness, which effects which path it takes at the sorting bifurcation. As droplets approach a bifurcation junction, they are exposed to velocity gradients that result in shear gradients. These shear gradients apply a lateral force that can direct them to different outlets from where the flow lines would normally carry them. When droplets of different sizes but similar stiffness are exposed to the shear gradients, the method can separate out different size droplets—as shown in the prior art.

Applicants' method will exploit the fact that given droplets of similar size but different stiffness, the "softer" droplets deform more than the stiffer ones reducing the lateral force exerted upon them, and hence their ability to move into the sort channel. For droplets that have large assembled molecular or polymer products, the large molecules result in a change in the droplet's overall stiffness. The overall change in droplet stiffness varies roughly as a function of the ratio of the product to reactant concentration and the difference in the product to reactant molecular size. It is on this basis that Applicants' invention passively separates out the successful product producing droplets simply based on channel geometry design and flow rate control for a given droplet stiffness and viscosity.

EXAMPLE(S)

Figure 2:
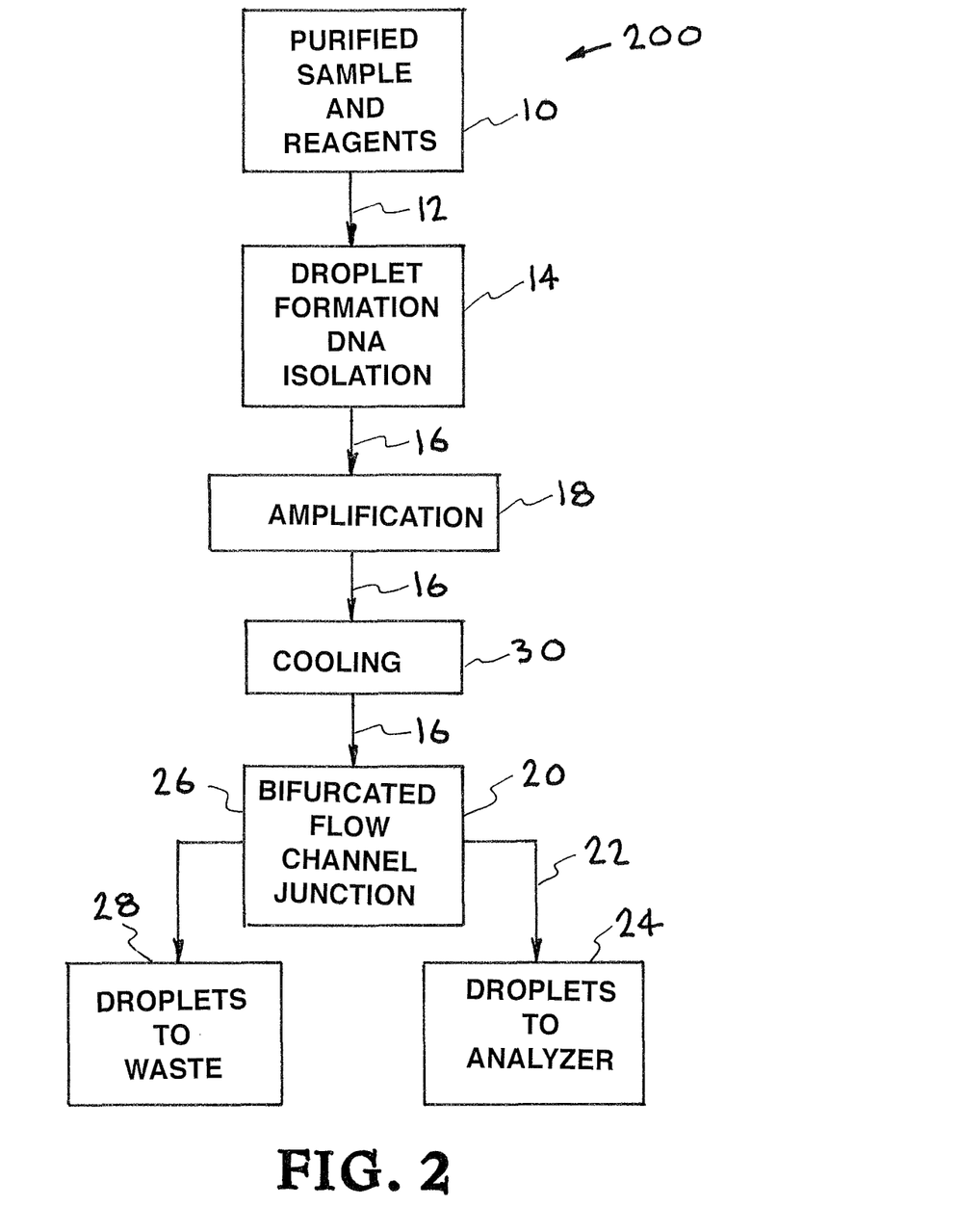
FIG. 2 is another flow chart illustrating components of system for sorting droplets.

In nucleic acid detection systems the starting concentration of targeted nucleic acids is typically unknown, and varies over many orders of magnitude. Additionally, the samples are run dilute to ensure that no droplets contain more than one starting copy to eliminate interference from similar genomic templates. Therefore many droplets are generated that contain no genetic material to amplify. The droplets are then run through a Polymerase Chain Reaction (PCR) zone (FIG. 2). The proposed sorting system will only select the droplets that have a sufficient quantity of post-amplified nucleic acid material to change the droplet's viscosity, and hence its stiffness, which effects which path it takes at the sorting bifurcation. As droplets approach a bifurcation junction, they are exposed to velocity gradients that result in shear gradients. These shear gradients apply a lateral force that can direct them to different outlets from where the flow lines would normally carry them. When droplets of different sizes but similar stiffness are exposed to the shear gradients, the method can separate out different size droplets. When droplets of similar sizes but different stiffness are exposed in these devices, the softer droplets deform more than the stiffer ones reducing the lateral force exerted upon it. For droplets that have PCR amplicons, the long chain DNA molecules result in a change in its overall stiffness. The overall change in droplet stiffness will vary as a function of the total number of DNA copies synthesized and their respective chain length. It is on this basis that Applicants' invention will passively separate out the PCR amplicons simply based on channel geometry design and flow rate control.

Figure 1:
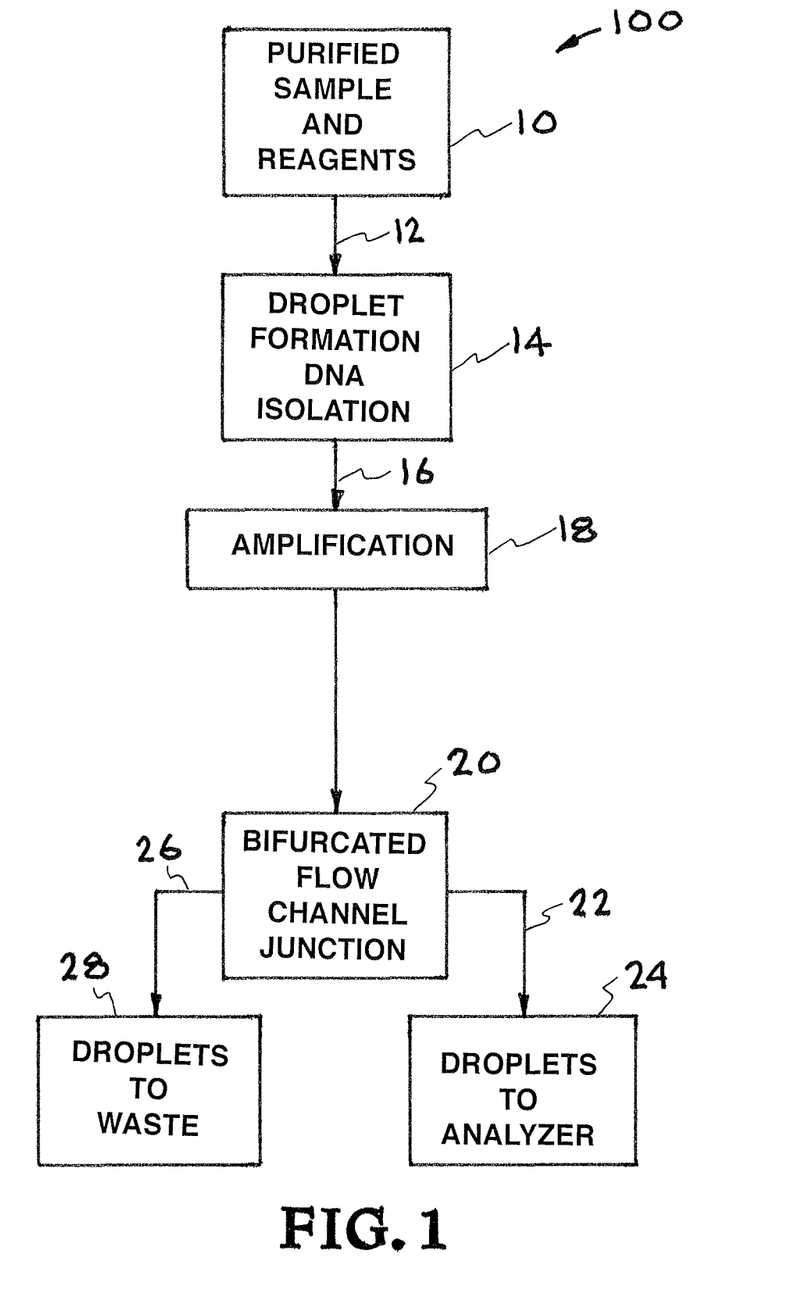
FIG. 1 is a flow chart illustrating components of a chip-based system for sorting droplets.

FIG. 1 is a flow chart describing the items on a chip-based method and system for sorting droplets. The overall system is labeled 100.

In step one purified sample and reagents are carried by channel 12 to step two where droplet formation and DNA isolation occur. Droplets of uniform size are formed during step two and enter channel 16. The channel 16 is filed with a carrier fluid that does not mix with the droplets therefore the droplets are carried along in channel 16 at space intervals. Some droplets contain DNA and some are empty. The droplets proceed along the channel 16 to step three 18 where amplification takes place. After amplification has taken place the droplets containing DNA will have become stiffer than those droplets containing no DNA. The droplets now continue along the channel 16 to step four 20. In step four the droplets enter a bifurcated flow channel with branching arms 22 and 26 of different sizes. The different sizes of the arms of the bifurcated flow channel will cause the pressure to be greater in one of the arms 26 than in the other arm 22. This pressure differential will cause the stiffer droplets to enter the arm 22 with less pressure and the essentially empty droplets being less stiff will be able to slightly distort and pass through the arm 26 that has the higher pressure. The stiffer droplets that have entered arm 22 will proceed to the droplet analyzer 24. The empty droplets that have entered arm 26 will go to droplet waste 28.

FIG. 2 is another flow chart describing the items on a chip-based method and system for sorting droplets. The overall system is labeled 200. This system 200 is essentially the same as the system described in FIG. 1. The difference in the system 200 is that an additional step has been added between steps three and four of FIG. 1. The new step of system 200 will become step three and the step four of FIG. 1 will now be called step five. This new step three of system 200 consists of a cooling step which will further increase the stiffness of the droplets of interest. The droplets will then be processed as described in FIG. 1.

Figure 3:
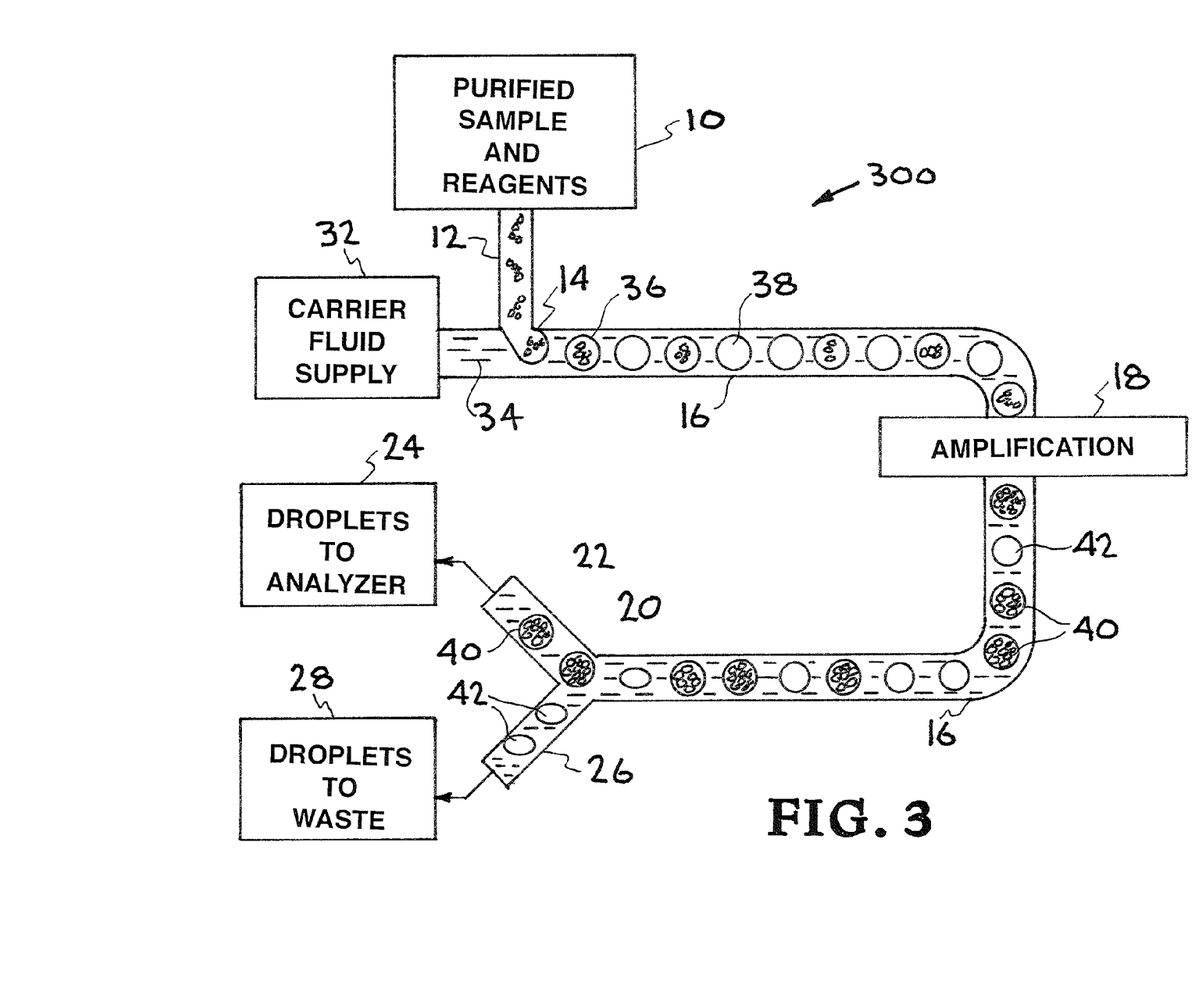
FIG. 3 is a schematic of the chip-based system for sorting droplets of FIG. 1.

FIG. 3 is a schematic of the chip-based method and system for sorting droplets of FIG. 1. The same reference numerals of items from FIG. 1 will be used to identify the same items in the schematic of FIG. 3 with the addition of items 32 the carrier fluid supply, 32 the carrier fluid, 36 droplets containing material, 38 droplets with no material, 40 amplified droplets and empty droplets. The overall schematic is labeled 300. The system 300 here described starts with the purified sample and reagents entering the channel 12 and proceeding to 14 the droplet formation and DNA isolation step. The created droplets of uniform size are now in channel 16 which is filled with carrier fluid 34 supplied from carrier fluid supply 32. The droplets some with material labeled 36 and the droplets with no material labeled 38 now proceed along the channel 16 to the amplification step 18. After the amplification step the droplets containing material, previously, labeled 36 will have become stiffer due to the increased material in the droplet, the droplet is now labeled 40 and the droplets containing no material are now labeled 42. The droplets now travel along channel 16 to the bifurcated flow channel junction 20 where the stiffer droplets 40 will be induced to enter arm 22 and the droplets 40 will proceed to droplet analyzer 24. The empty droplets 42 being less stiff than the droplets 40 will be able to distort slightly and enter arm 26 and proceed to the droplet waste 28. The droplets traveling along channel 16 and through the bifurcated flow channel junction 20 are separated based upon the degree of stiffness of the droplets. The separator includes an inlet to said second flow channel 22 with the inlet having a diameter that is less than the diameter of the droplets 42. The main flow channel 16 has a main flow channel pressure and the second flow channel 26 has a second flow channel pressure with said the flow channel 26 pressure being less than the main flow channel 16 pressure.

Figure 4:
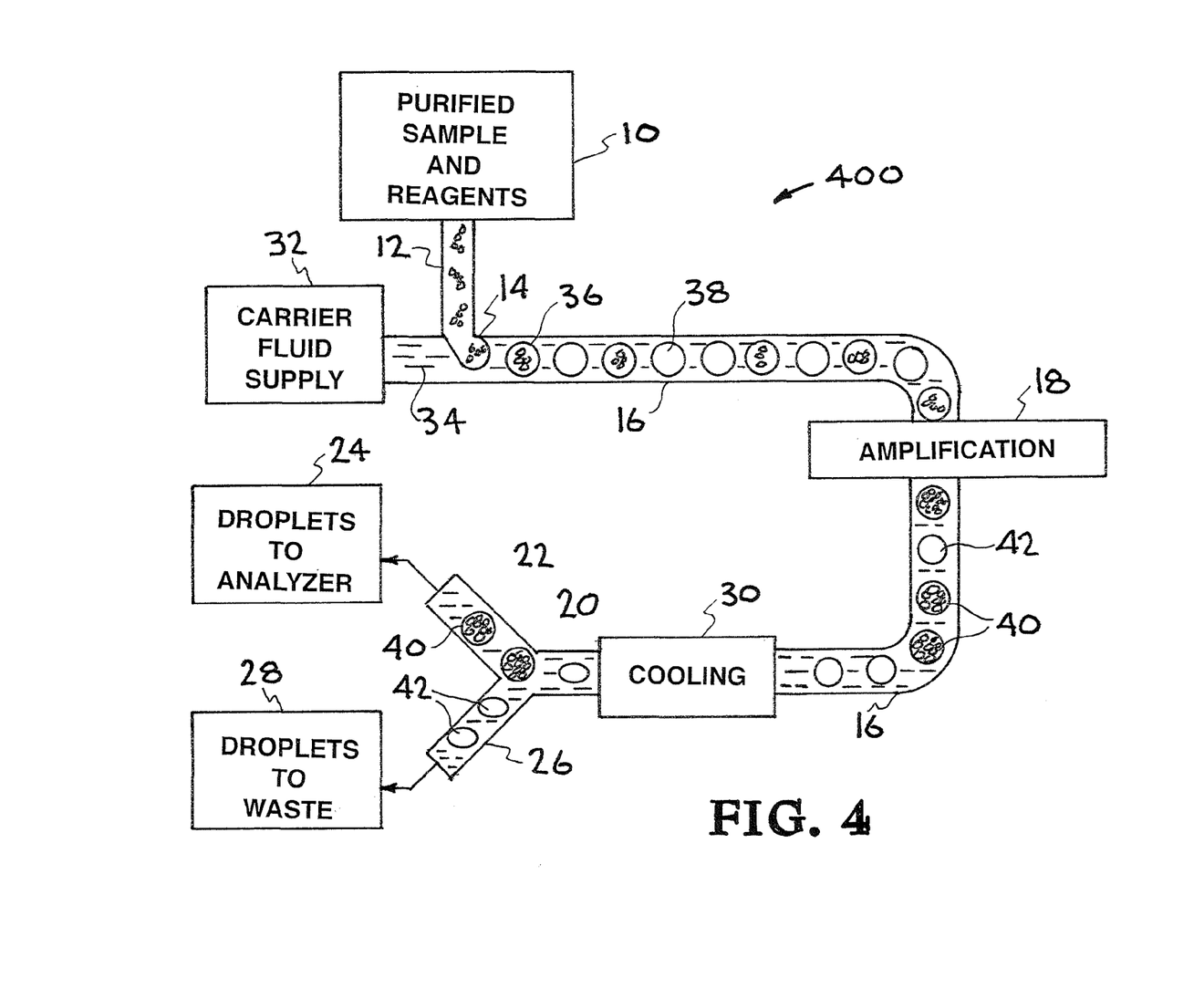
FIG. 4 is another schematic illustrating the chip-based system for sorting droplets.

FIG. 4 is another schematic illustrating the chip-based method and system for sorting droplets. The overall system is labeled 400. The system illustrated here is just like the system 300 previously described except for the addition of a cooling station 30. This cooling station 30 will add stiffness to the droplets that have been amplified thus enhancing the ability to sort full droplets from empty droplets.

Figure 5:
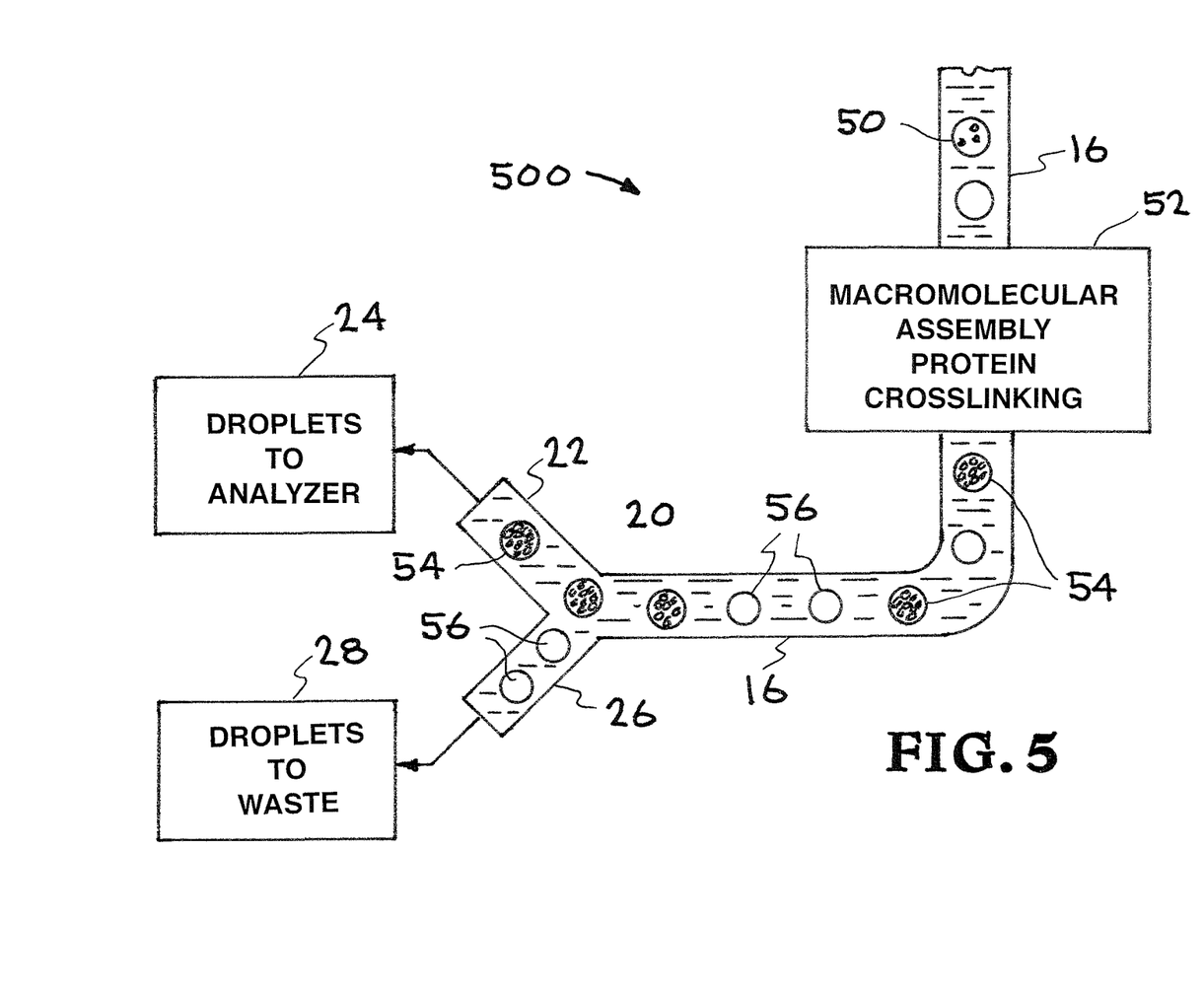
FIG. 5 is a chip-based method and system for protein crosslinking for viscous sorting.

Referring now to FIG. 5, a schematic of a chip-based method and system for macromoleculear assembly, specifically, protein crosslinking is shown. The overall system is designated generally by the reference numeral 500. The same reference numerals of items used in FIG. 1 are also used to identify the same items in the schematic of FIG. 5. Proteins produced by tissues and cells can be cross-linked using synthetic or natural cross-linking agents to form long macromolecular structures.

The protein crosslinking system 500 begins with droplet containing sample 50 entering the channel 16 and proceeding to the macromoleculear assembly, protein crosslinking step 52. The channel 16 is filled with a carrier fluid. Note that empty droplets are also in channel 16.

In the macromolecular assembly step 52, proteins produced by tissues and cells are cross-linked using synthetic or natural cross-linking agents to form long macromolecular structures. This produces the enhanced sample droplets 54. The enhanced sample droplets 54 and the empty droplets labeled 56 enter channel 16. The enhanced sample droplets 54 are stiffer than the empty droplets labeled 56 because the enhanced sample droplets 54 contain the enhanced sample.

The enhanced sample droplets 54 and the empty droplets 56 now proceed along the channel 16 to the separation step. The droplets containing material labeled 54 are stiffer than the empty droplets 56 due to the material in the droplets 54. The enhanced sample droplets 54 and the empty droplets 56 travel along channel 16 to the bifurcated flow channel junction 20 where the stiffer droplets 54 will be induced to enter arm 22. The stiffer droplets 54 will proceed to droplet analyzer 24 or other processing. The empty droplets 56 being less stiff than the droplets 54 will be able to distort slightly and enter arm 26 and proceed to the droplet waste 28.

Figure 6:
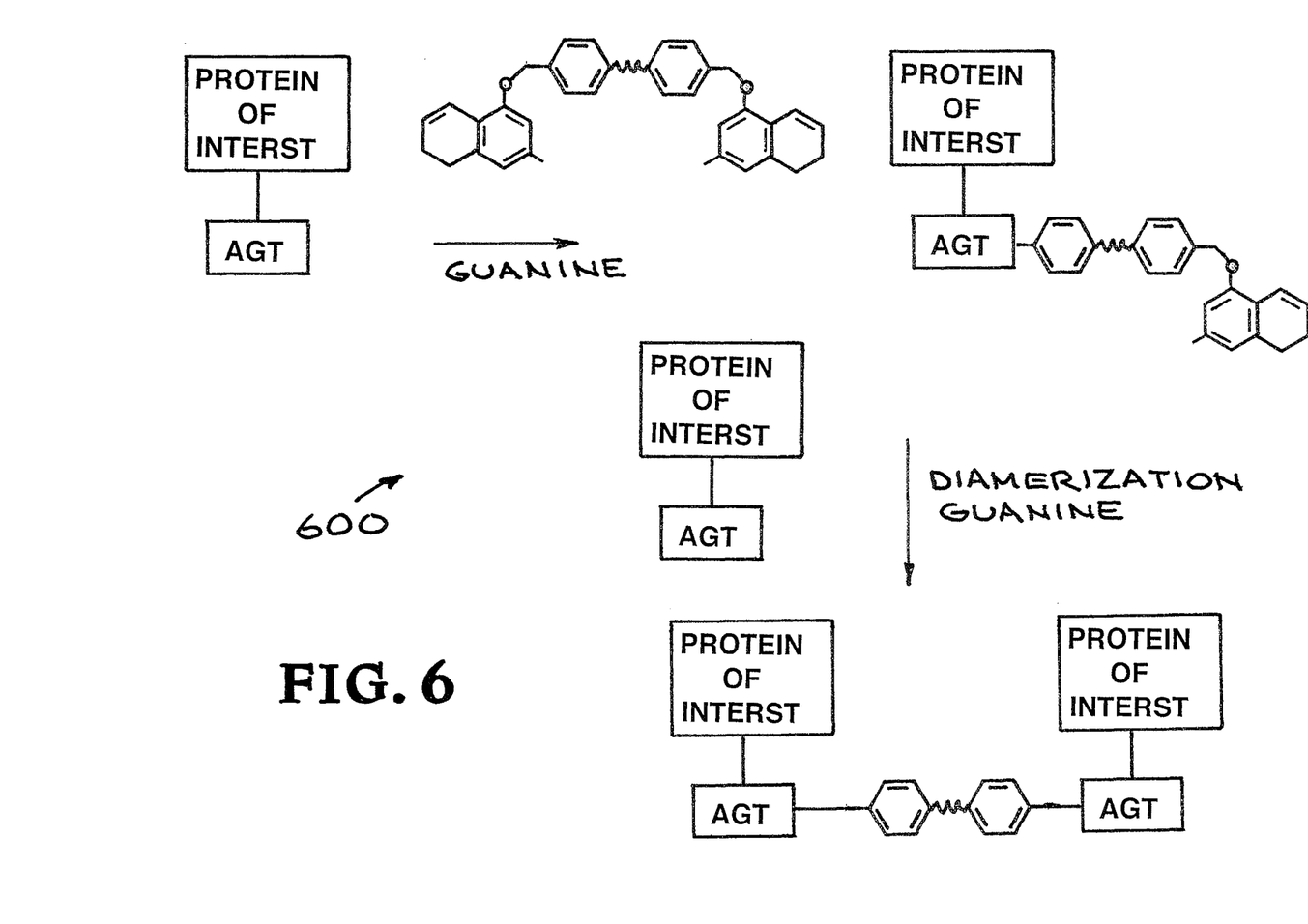
FIG. 6 is a flow chart of macromolecular assembly.

Referring now to FIG. 6, a flow chart of the macromolecular assembly protein crosslinking step 52 of FIG. 5 is shown. Proteins produced by tissues and cells can be cross-linked using synthetic or natural cross-linking agents to form long macromolecular structures. The five journal articles identified below described some examples of protein crosslinking for viscous sorting. The five journal articles identified below are incorporated herein in their entirety for all purposes.

Article 1—"Photo-leucine and photo-methionine allow identification of protein-protein interactions in living cells;" by Suchanek, M., Radzikowska, A. & Thiele, C.; Nat Meth 2, 261-268 (2005).

Article 2—"Metal-Mediated Self-Assembly of Protein Superstructures: Influence of Secondary Interactions on Protein Oligomerization and Aggregatio," by Salgado, E. N., Lewis, R. A., Faraone-Mennella, J. & Tezcan, F. A.; Journal of the American Chemical Society 130, 6082-6084 (2008).

Article 3—"The cross-linking of proteins with glutaraldehyde and its use for the preaparation of immunoadsorbernts;" by Avrameas, S. & Ternynck, T.; Immunochemistry 6, 53-66 (1969).

Article 4—"Inducing and Sensing Protein-Protein Interactions in Living Cells by Selective Cross-linking;" by Lemercier, G., Gendreizig, S., Kindermann, M. & Johnsson, K.; Angewandte Chemie International Edition 46, 4281-4284 (2007).

Article 5—"Self-assembly and cross-linking of bionanoparticles at liquid-liquid interfaces;" by Russell, J. T. et al.; Angewandte Chemie—International Edition 44, 2420-2426 (2005).

Protein-protein interactions are the key to organizing cellular processes in space and time. The only direct way to identify such interactions in their cellular environment is by photo-cross-linking. The macromolecular assembly step 52 produces the enhanced sample droplets 54.

Figure 7:
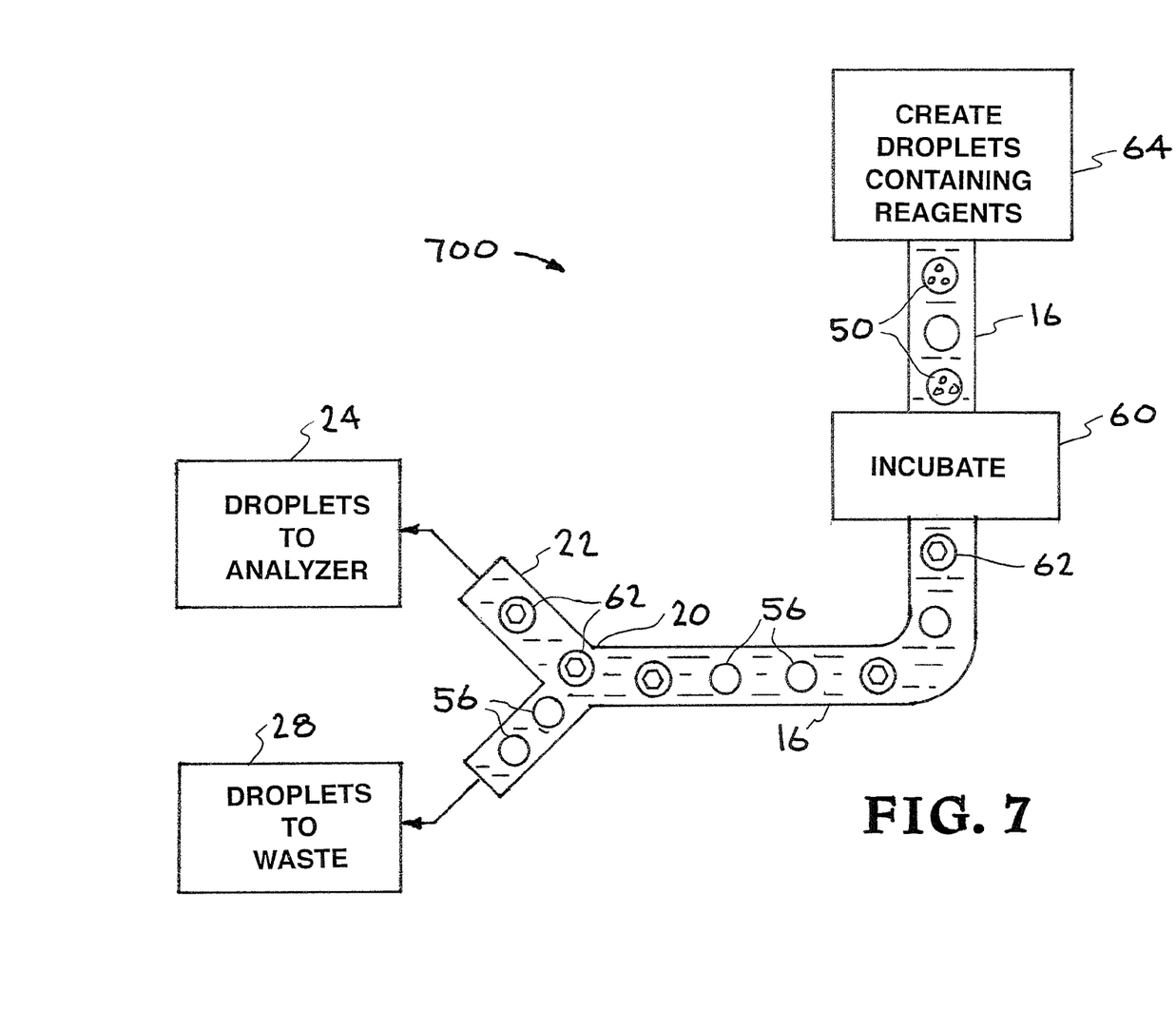
FIG. 7 is a schematic of a system for protein crystallography sorting.

Referring now to FIG. 7, a schematic of a system for protein crystallography sorting is shown. The overall system is designated generally by the reference numeral 700. The same reference numerals of items from FIG. 1 are used to identify the same items in the schematic of FIG. 7.

A droplet generator 64 produces droplets 50 containing reagents for producing crystals. For example, the droplet generator 64 can be a droplet generator that uses a variety of reagents for producing crystals for X-ray crystallography. The droplets 50 need to incubate in order to determine which droplets and reagent mix will successfully produce crystals.

The droplets 50 produced by the droplet generator 64 proceed to the incubate step 60. In the incubation step 60, some of the droplets have produced droplets with crystals 62 and some of the droplets 56 have not produced crystals. The droplets containing crystals 62 are stiffer than the empty droplets 56 due to the crystal material in the droplets 62. The droplets 62 and 56 travel along channel 16 to the bifurcated flow channel junction 20 where the stiffer droplets 62 will be induced to enter arm 22. The stiffer droplets 62 will proceed to droplet analyzer 24 or other processing. The empty droplets 56 being less stiff than the droplets 54 will be able to distort slightly and enter arm 26 and proceed to the droplet waste 28.

Figure 8:
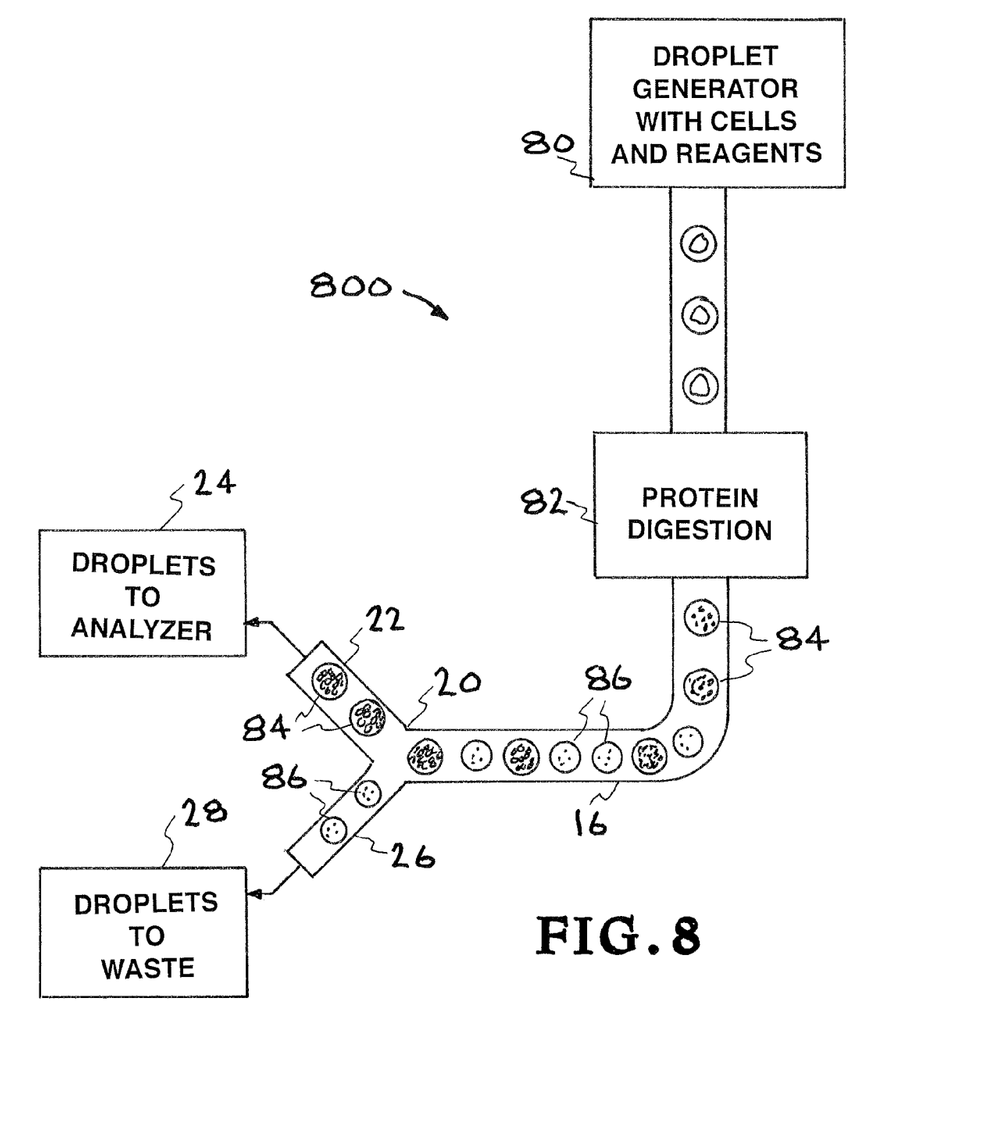
FIG. 8 is a schematic of a system for protein digestion sorting.

Referring now to FIG. 8, a schematic of a system for protein digestion sorting is shown. The overall system is designated generally by the reference numeral 800. The same reference numerals of items from FIG. 1 are used to identify the same items in the schematic of FIG. 8.

The system 800 starts with droplet generator 80 producing droplets which enter the channel 16 and proceeding to the protein digestion step 82. The droplets entering the protein digestion step 82 contain cells, virions, or other degradable structures. The droplet are processed in step 80 which produces droplets 84 and 86. The droplets 84 contain more stiffness-enhancing material such as large intact cells or other digestible material and are stiffer than the droplets 86 that contain no cells or completely broken down material because the large and intact material in the droplets 84 makes them stiffer.

The droplets 84 and 86 travel along channel 16 to the bifurcated flow channel junction 20. The bifurcated flow channel junction 20 acts as a sorter to separate droplets 84 from droplets 86. The stiffer droplets 84 will enter arm 22 and proceed to droplet analyzer 24 or other processing. For example, if the aims of the sorter channel junction 20 are to accumulate the digestion enzymes that work on the cells, accumulate the digestion products from within the broken cells, or harvest desired cellular contents if the cells are being used as bio-reactors, then the stiffer droplets 84 will correspond to intact cells, whereas droplets with the broken down cells will be less stiff and be the desired product sent to droplet analyzer 28 or other processing.

The droplets 86 being less stiff than the droplets 84 will be able to distort slightly and enter arm 26. The droplets 86 will proceed to droplet analyzer 28 or other processing. For example, if the aims of the sorter channel junction 20 are to collect the cells that don't get digested (i.e. test for specific antigens, antibodies, or identification of the bacteria/cell type) these undigested cell droplets 84 will go to analyzer 24 or other processing.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for passive sorting of droplets, comprising:
a chip,
a main flow channel in said chip,
a source of carrier fluid connected to said main flow channel that fills said main flow channel with said carrier fluid and provides a fluid pressure,
a source containing a sample and reagents,
a sample and reagents channel connected to said source and connected to said main flow channel wherein said sample and said reagents and said sample and reagents channel form droplets of said sample and said reagents and provide a flow stream of said droplets in said main flow channel,
an amplification zone in said main flow channel that receives said flow stream of said droplets and provides polymerase chain reaction of said sample in said droplets producing first droplets containing DNA and second droplets that do not contain DNA and are therefore empty wherein said first droplets and said second droplets have substantially the same diameter and wherein said first droplets containing DNA have a first degree of stiffness and wherein said second droplets that are empty have a second degree of stiffness that is less than said first degree of stiffness, a bifurcated flow channel junction connected to said main flow channel in said chip, a first separator flow channel connected to said bifurcated flow channel junction that has a size that provides less fluid pressure and causes said first droplets containing DNA and a first degree of stiffness to flow through said first separator flow channel, and a second separator flow channel connected to said bifurcated flow channel junction that has a size that provides higher pressure and causes said second droplets that are empty and have a second degree of stiffness that is less than said first degree of stiffness to flow through said second separator flow channel thereby providing a separator for separating said second droplets that are empty and have a second degree of stiffness that is less than said first degree of stiffness from said first droplets containing DNA and directing said second droplets into said second separator flow channel.

2. The apparatus for passive sorting of droplets of claim 1 wherein said carrier fluid and said sample and said reagents are materials that do not mix thereby producing said droplets wherein said droplets are in the form of microreactors.

3. The apparatus for passive sorting of droplets of claim 1 wherein said DNA in said droplets is protein DNA having protein DNA molecular structures.

4. The apparatus for passive sorting of droplets of claim 1 wherein said DNA in said droplets is protein DNA having protein DNA macromolecular structures.

5. The apparatus for passive sorting of droplets of claim 1 further comprising a cooling zone in said main flow channel between said amplification zone and said bifurcated flow channel junction.

6. The apparatus for passive sorting of droplets of claim 1 wherein said DNA in said droplets is cell DNA.

7. The apparatus for passive sorting of droplets of claim 1 wherein said bifurcated flow channel junction includes an inlet to said second separator flow channel with said inlet having a diameter that is less than the diameter of said second droplets.

8. An apparatus for passive sorting of droplets, comprising:
a main flow channel, a source of carrier fluid connected to said main flow channel that fills said main flow channel with said carrier fluid and provides a fluid pressure, a droplet generator that produces droplets containing reagents for producing crystals and forms droplets of said reagents in said carrier fluid providing a flow stream of droplets in said main flow channel, an incubate zone in said main flow channel that receives said flow stream of said droplets and provides incubation of said reagents in said droplets producing first droplets containing crystals and second droplets that do not contain crystals and are therefore empty wherein said droplets have substantially the same diameter and wherein said flow stream of droplets includes first droplets containing crystals having a first degree of stiffness and second droplets that are empty having a second degree of stiffness that is less than said first degree of stiffness, a bifurcated flow channel junction connected to said main flow channel, a first separator flow channel connected to said bifurcated flow channel junction that has a size that provides less fluid pressure and causes said first droplets containing crystals and have a first degree of stiffness to flow through said first separator flow channel, and a second separator flow channel connected to said bifurcated flow channel junction that has a size that provides higher pressure and causes for said second droplets having a second degree of stiffness that is less than said first degree of stiffness to flow through said second separator flow channel for separating said second droplets from said first droplets and directing said second droplets having a second degree of stiffness that is less than said first degree of stiffness into said second separator flow channel.

9. The apparatus for passive sorting of droplets of claim 8 wherein said carrier fluid and said reagents are materials that do not mix thereby producing said droplets containing reagents that are microreactors.

* * * * *